(12) United States Patent
Rust (10) Patent No.: US 8,876,883 B2
(45) Date of Patent: Nov. 4, 2014

(54) SELF-FLARING ACTIVE FIXATION ELEMENT FOR A STENT GRAFT

(75) Inventor: Matthew Rust, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1109 days.

(21) Appl. No.: 12/429,386

(22) Filed: Apr. 24, 2009

(65) Prior Publication Data

US 2010/0274345 A1 Oct. 28, 2010

(51) Int. Cl.
*A61F 2/07* (2013.01)
*A61F 2/90* (2013.01)
*A61F 2/89* (2013.01)
*A61F 2/848* (2013.01)
*A61F 2/06* (2013.01)

(52) U.S. Cl.
CPC ........... *A61F 2/07* (2013.01); *A61F 2230/0019* (2013.01); *A61F 2002/8486* (2013.01); *A61F 2002/061* (2013.01); *A61F 2/90* (2013.01); *A61F 2/89* (2013.01); *A61F 2002/8483* (2013.01); *A61F 2220/0016* (2013.01); *A61F 2230/0026* (2013.01)
USPC ........................................ 623/1.14; 623/1.36

(58) Field of Classification Search
USPC ...................... 623/1.13, 1.14, 1.36
See application file for complete search history.

(56) References Cited

U.S. PATENT DOCUMENTS

| | | | |
|---|---|---|---|
| 4,140,126 A | 2/1979 | Choudhury et al. | |
| 4,617,932 A | 10/1986 | Kornberg | |
| 5,158,548 A | 10/1992 | Lau et al. | |
| 5,514,154 A | 5/1996 | Lau et al. | |
| 5,562,728 A | 10/1996 | Lazarus et al. | |
| 5,603,721 A | 2/1997 | Lau et al. | |
| 5,720,776 A | 2/1998 | Chuter | |
| 5,728,158 A | 3/1998 | Lau et al. | |
| 5,735,893 A | 4/1998 | Lau et al. | |
| 5,766,238 A | 6/1998 | Lau et al. | |
| 5,800,526 A * | 9/1998 | Anderson et al. | 623/1.16 |
| 5,925,061 A | 7/1999 | Ogi et al. | |
| 6,056,776 A | 5/2000 | Lau et al. | |
| 6,066,167 A | 5/2000 | Lau et al. | |
| 6,066,168 A | 5/2000 | Lau et al. | |
| 6,096,071 A | 8/2000 | Yadav | |
| 6,210,435 B1 | 4/2001 | Piplani | |
| 6,221,102 B1 | 4/2001 | Baker | |

(Continued)

FOREIGN PATENT DOCUMENTS

| | | |
|---|---|---|
| EP | 1880693 | 1/2008 |
| WO | WO03/099108 | 12/2003 |

*Primary Examiner* — Thomas J Sweet
*Assistant Examiner* — Megan Wolf (57) ABSTRACT

A stent graft includes a stent graft material of tubular shape and annular shaped stent elements coupled to the stent graft material. The stent graft further includes hooked fixation elements, having hook-end portions and coupling-end, circumferentially spaced about an annular shaped spring attachment element, and coupled to the stent graft at apexes of the spring attachment element. Before deployment the hook-end portions of the apexes of the attachment element and the hooked fixation elements attached thereto are compressed within the space bounded by the interior and exterior sides of the spring attachment element and angled laser cut strut inner surfaces under each apex of the spring attachment element are cut at an angle to cause apex and hook rotation at expansion and deployment. At deployment, the apex and hook-end portions rotate outwardly from the stent graft, partially penetrating the body vessel walls in which the stent graft is deployed and actively fixing the stent graft at the position of deployment.

19 Claims, 6 Drawing Sheets

(56) References Cited

U.S. PATENT DOCUMENTS

| | | |
|---|---|---|
| 2003/0220683 A1 | 11/2003 | Minasian |
| 2005/0240259 A1 | 10/2005 | Sisken et al. |
| 2007/0038288 A1* | 2/2007 | Lye et al. .................... 623/1.16 |
| 2008/0021544 A1* | 1/2008 | Majercak et al. ............ 623/1.36 |

* cited by examiner

SELF-FLARING ACTIVE FIXATION ELEMENT FOR A STENT GRAFT

FIELD OF THE INVENTION

The present invention relates generally to endoluminal stent grafts and more particularly to an active structure for fixing endoluminal stent grafts within body vessels.

BACKGROUND OF THE INVENTION

A stent graft typically includes radially expandable stents, a plurality of annular stent rings forming a cylindrical reinforcement structure, and a cylindrically shaped graft material to which the stent rings are coupled. Stent grafts are well known to be used in acting as reinforced grafts which are delivered by a catheter and deployed to bypass a damaged diseased portion of an arterial body vessel (lumen).

At deployment, after insertion and transluminal transport to the point of use within a damaged or diseased body vessel, e.g., an aneurysmal location in an artery, the stent graft is radially expanded. A stent graft is typically self-expanding or balloon expandable by application of pressure applied outwardly from the interior of the stent graft. After deployment, the ends of the stent graft seal against healthy portions of the body vessel to provide a seal upstream and downstream of the damaged (diseased) portion being bypassed.

To avoid leakage around the seal between the stent graft and vascular wall at the stent graft and to avoid other complications associated with migration of a stent graft, it is important to assure that stent grafts maintained fixation within a body vessel at the location of initial deployment. Two basic approaches have been developed to improve fixation of stent grafts at the location of initial deployment.

A first approach to stent graft fixation, sometimes referred to as passive fixation, relies on providing the stent graft with an outward biasing radial force at the contact interface between the stent graft and the interior wall of the body vessel in which it was deployed. Typically, a radial force, biasing toward the interior wall of the body vessel, is supplied by a spring attachment element at one or both ends of the tubular stent graft. The spring attachment element urges the stent graft into abutting contact with the interior wall of the body vessel where frictional forces between the spring attachment element and the vessel interior wall provide a substantial portion of the forces needed to create both a liquid-tight seal between the stent graft and the body vessel and fixation of the stent graft at its location of initial deployment.

However, with this first approach, the radial biasing force provided by the spring attachment element has to be carefully selected. A body vessel's capacity to resist a continuous outward radial force is limited. Excessive outward radial force on the interior wall of a body vessel could cause excess bulging and damage to the body vessel. Also, in cases where the contact interface, sometimes called the landing zone, between the stent graft and the body vessel is small (short), the surface area on the interior of the body vessel available to resist outward radial force of the stent graft may be insufficient to firmly and permanently affix the stent graft. An abdominal aortic aneurysm with a short neck landing zone is an example where insufficient area for application of radial force may be available to affix a stent graft.

A second approach to stent graft fixation, sometimes called active fixation, relies on providing the stent graft with hooked and/or spiked fixation elements which extend laterally outwardly from the stent graft to mechanically engage and/or partially penetrate the interior wall of the body vessel. Typically, multiple fixation elements are located circumferentially about annular structures attached to one or both ends of the tubular stent graft.

However, with this second approach it is often difficult to contain the laterally extending fixation elements within a conventional flexible sheath, well known to those of skill in the art, used for containing a compressed stent graft prior to deployment. The laterally extending fixation elements can act as impediments to smooth deployment of the stent graft within a body vessel as the exposed fixation elements can drag on the interior wall of the catheter and resist sliding prior to being deployed in the body vessel. Leakage through the stent graft seal with the wall of the body vessel occurs if a good liquid-tight seal between the stent graft and the interior wall of the body vessel is not effected by the fixation elements alone without the outward radial force provided by the spring attachment element of the passive fixation approach. Further, the chance of migration of the stent graft is nearly eliminated by the use of hooks or other lateral protrusions when they land in healthy tissue.

What is needed is a stent graft that provides secure fixation and sealing using both passive and active means. Such a stent graft should have a controlled outward biasing radial force and no or reduced impediments to the smooth endoluminal placement of the stent graft.

SUMMARY OF THE INVENTION

A stent graft according to the invention includes a graft material of tubular shape and laser cut annular stent elements making up a cylindrical reinforcing framework coupled to the graft material. The stent elements include hooked fixation elements, having hook-end portions and coupling-end, circumferentially spaced about an upper annular spring attachment element coupled to the upper end of the stent.

The upper annular spring attachment element is configured in a serpentine pattern, thus it has upper and lower apexes interconnected by struts. Each coupling-end portion of the hooked fixation elements is attached to one of the upper apexes of the upper spring attachment element such that, prior to deployment in a body vessel, the hooked fixation elements lie essentially within a projected wall of cylindrically shaped tubular space defined by the interior and exterior sides of the annular upper spring attachment element of the stent graft. In one example, the hooked fixation elements include one or more barbs or sharp ends to enhance attachment to the inner wall of the body vessel at deployment of the stent graft.

In one example, struts making up a part of the upper spring attachment element are laser cut from tubular base material and formed in such a way that the apexes and struts have a horizontal inner arc radius at the side of the apex and strut facing in, that is less than a horizontal outer arc radius at the side of the apex and strut facing out. The horizontal cross sectional of a strut connected to an apex could vary from being an isosceles trapezoid to being nearly triangularly shaped depending on an angle α laser cut below the strut to form an inside surface of the strut under the apex with the largest (longest) parallel sides of adjacent the trapezoid on each strut face each other.

Prior to deployment, the hooked fixation elements lie essentially within the annular space defined and bounded by the interior and exterior sides of the annular shaped upper spring attachment element of the stent graft (tubular cylindrical wall thickness). Prior to deployment the hook-end portions of the hooked fixation elements neither extend in toward the interior of the stent graft, nor flare outwardly toward the exterior of the stent graft, from the space defined by the upper annular spring attachment element of the stent graft. Since the hooked fixation elements do not flare outwardly when the stent elements are in their compressed configuration, the hooked fixation elements do not present impediments to the smooth deployment of the stent graft at the point of use of the stent graft within the body vessel.

During deployment, when the stent and upper spring attachment element expand or are radially expanded, the upper apexes connected to the struts forming the upper spring attachment element, and, the hooked fixation elements coupled to the upper apexes, are designed to twist toward the exterior of the stent graft, flare outwardly from the tubular shape of the expanded stent graft, and partially penetrate the inner walls of the body vessel in which the stent graft is deployed, thereby actively fixing the stent graft, at its upper end, to the body vessel.

During expansion at deployment, the large amount of strut material at the surface facing the adjacent strut and the neutral bending axes of the adjacent struts and their connection to a common apex (at one end of the strut resists deformation more than the relatively smaller amount of strut material away from the center of the apex), thereby effecting the outward twist of the struts and the upper apexes, and the hooked fixation elements coupled thereto. The struts and upper apexes strain and deform by twisting to redistribute and lower the stress induced in the struts during radial expansion of the stent graft. The degree of apical twisting is controlled by adjusting the diagonal angle α of the strut's inner laser cut surface at the side of strut facing the adjacent strut extending from a common apex.

By making the angle α of the stent diagonal surface with respect to the apex centerline, the apex will rotate as a result of being tied at an angle to a common apex and as a result of the geometric orientation of the cross-sectional area which is subject to stress and deformation as deployment takes place. The additional material in the inner portion of the strut (along its longest surface) resists deformation more than the material at the outer edge of the strut and apex relative to the angle of the diagonal cut establishing the angle with respect to a radius of the stent graft facilitating the rotation of the apex upon expansion. By attaching the struts to the apex it can rotate with its hook to impinge the vessel wall. The hook also folds into the confines of the projection of the wall thickness of the hollow cylindrical wall defined by the stent ring when it is constrained.

Accordingly, use of a stent graft including self-flaring (self rotating)active fixation elements, provides secure fixation of the stent graft to the body vessel by both passive and active means. Also provided is a controlled radial biasing force by the spring attachment element and hooked and/or spiked fixation elements that present no impediment to the smooth intraluminal deployment of the stent graft.

DETAILED DESCRIPTION

Figure 1:
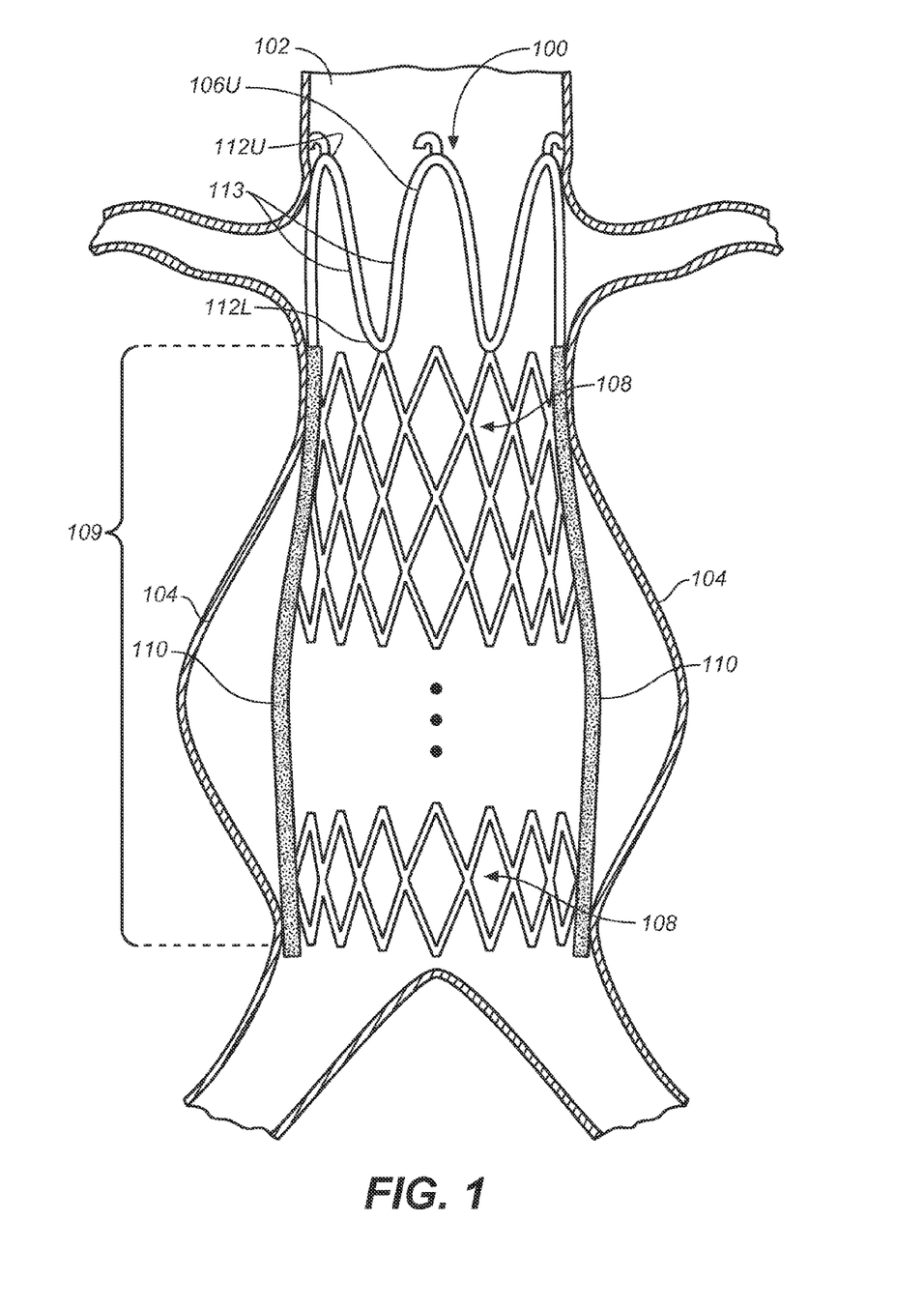
FIG. 1 is a partial cutaway view of a body vessel containing a stent graft, positioned and deployed for use.

FIG. 1 is a schematicized partial cutaway view of a body vessel 102 containing an aneurysm 104 excluded from body vessel 102 by a deployed stent graft 100 configured in accordance with the present invention.

Figure 2A:
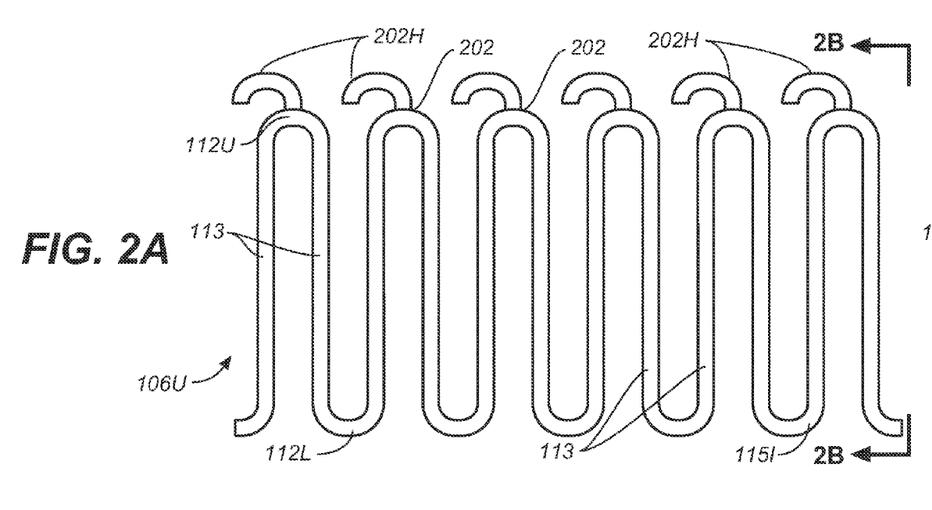
FIG. 2A is a schematicized before deployment, flat-layout, interior view of an upper spring attachment element (proximal spring) of the stent graft shown in FIG. 1 that includes self-flaring, active, hook fixation elements.
Figure 2B:
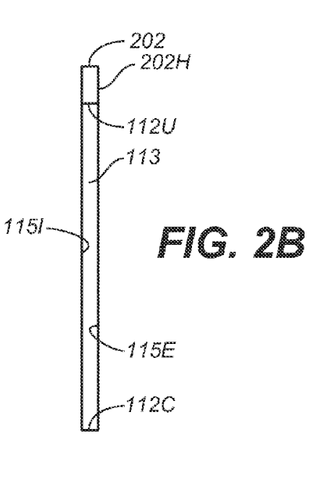
FIG. 2B is an end view of the upper spring attachment element shown in FIG. 2A.
Figure 2C:
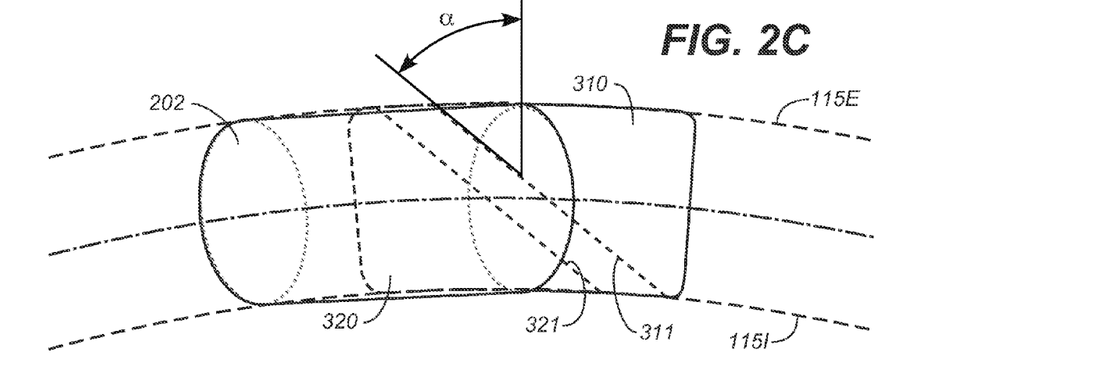
FIG. 2C is a schematicized top plan view of one upper apex of the upper spring attachment element of FIGS. 2A and 2B when the stent is in a compressed pre-deployment configuration.
Figure 2D:
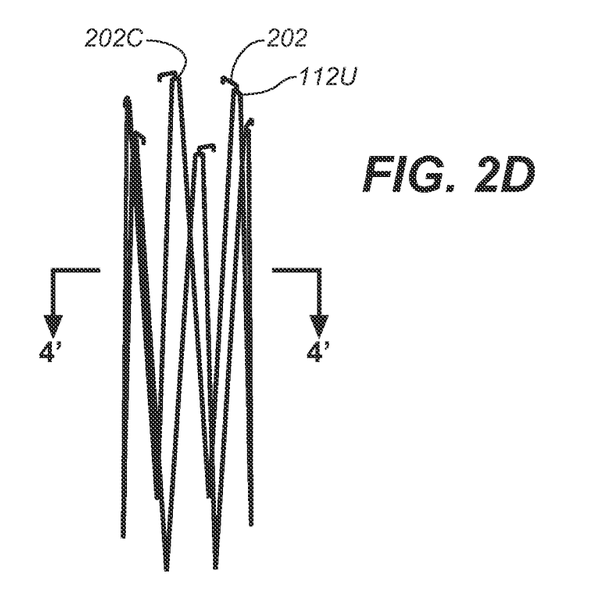
FIG. 2D is a schematicized perspective view of an upper spring attachment element (proximal spring) of the stent graft shown in FIG. 1 that includes self-flaring, active, hook fixation elements.

FIG. 2A is a schematicized before deployment flat-layout view and FIG. 2D is a schematicized perspective view of an upper spring attachment element 106U of stent graft 100 including self-flaring, active, hooked fixation elements 202. In use, stent graft 100 is generally configured in a tubular shape but, in FIG. 2A, upper spring attachment element 106U is shown in unfurled or flat-layout view for clarity of presentation.

FIG. 2B is a schematicized before deployment end view in the direction of 2B—2B of upper spring attachment element 106U shown in FIG. 2A.

Figure 2E:
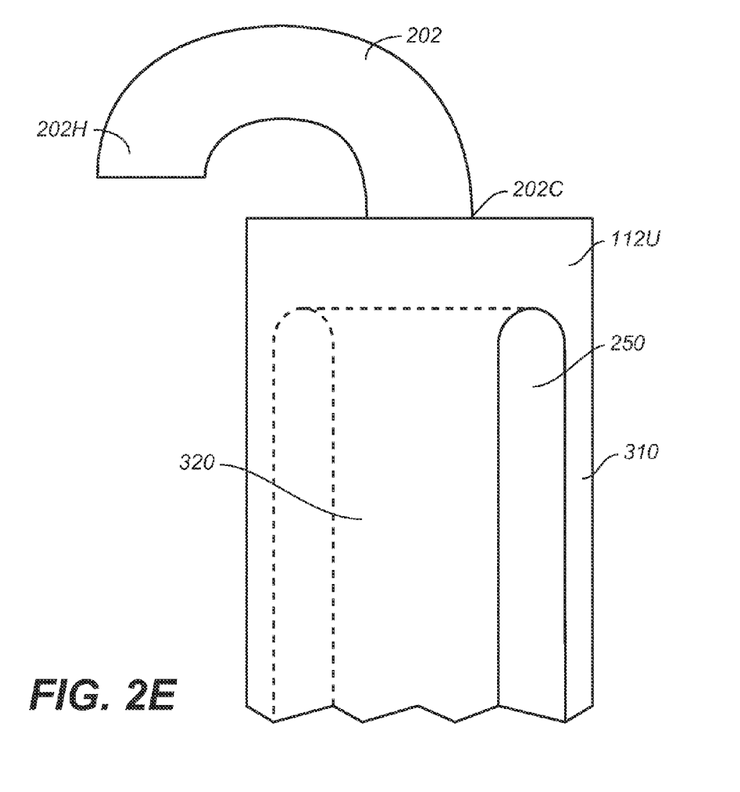
FIG. 2E is a schematicized side view of the upper apex shown in FIG. 2C.

FIG. 2C is a schematicized before deployment top plan view of one upper apex 112U of the upper spring attachment element 106U of FIGS. 2A and 2B. FIG. 2E is a schematicized side view of the of the upper apex shown in FIG. 2C;

Referring to FIGS. 1 and 2A-E together, a stent graft 100 includes a stent graft material 110 of tubular shape an annular shaped stent elements 108 making up one or more cylindrical reinforcing stent(s), e.g., 109, coupled to stent graft material 110.

Stent graft 100 further includes an upper, e.g., a first, spring attachment element 106U coupled to an end one of the plurality of stent elements 108 (FIG. 1) making up the cylindrical reinforcement structure, i.e. 109, of stent graft 100. Upper spring attachment element 106U forms an annulus of serpentine pattern having upper, e.g. first apexes, 112U and lower, e.g. second, apexes 112L interconnected by struts 113.

Stent graft 100 further includes hooked fixation elements 202 (FIGS. 2A, 2B, and 2C), having hook-end portions 202H and coupling-end 202C opposite hook-end portions 202H. Coupling-end 202C of hooked fixation elements 202 are integrally laser cut with or can alternately be coupled to upper spring attachment element 106U at upper apexes 112U by well know means such as welding.

As described more fully below, in one example, prior to deployment, coupling-end 202C of hooked fixation elements 202 are attached to upper apexes 112U of upper spring attachment element 106U such that hooked fixation elements 202 and, more particularly, hook-end portions 202H of hooked fixation elements 202, lie essentially within an annular shaped first space 201, defined and bounded by an interior side 115I and an exterior side 115E of compressed upper spring attachment element 106U. After deployment, hooked fixation elements 202 have rotated together with the apexes 112U and remain aligned with a radial axis of the rotated apexes 112U in a position outwardly from an annular shaped second space (established along a circumferential reference line), defined and bounded by interior side 115I and exterior side 115E of expanded upper spring attachment element 106U. In this position the hooked fixation element 112U has the opportunity to partially penetrate the inner wall of body vessel 102 in which stent graft 100 is deployed.

More particularly, in one example, upper apexes 112U twist (rotate) during the deployment expansion process. The degree and direction of twist in each upper apex 112U are designed to be uniform at the full radial expansion of stent graft 100 at deployment. Thus, by coupling hooked fixation elements 202 at upper apexes 112U, hooked fixation elements 202 are made to lie within the cylindrical wall band set by the radial thickness of the undeployed stent elements, prior to deployment, and to cause the upper apexes 112U and the hooks attached thereto to flare outwardly after expansion of stent graft 100 effects a twist to upper apexes 112U at deployment.

Illustratively, before deployment (FIGS. 2A-E) within body vessel 102, the stent graft 100 is confined to a compressed configuration, hooked fixation element 202 is coupled, at coupling-end 202C, to upper apex 112U of upper spring attachment element 106U such that hook-end portion 202H of hooked fixation element 202 lies in the projection of the cylindrical wall band upwards from the attachment element, defined by interior side 115I and exterior side 115E of compressed upper spring attachment element 106U, as shown in FIG. 2C.

The sides of the parallelogram shaped upper apex 112U are laser cut by a radial cut from circular tubing. The hook fixation element 202, while shown as a curved substantially circular cross section rod, can also be a partially or fully rectangular cross section which is easily cut using conventional stent laser cutting apparatus. While substantially square corners are shown, the corners may be rounded, by cutting or other conventionally known processing steps. Stent struts 310, 320 connecting to the bottom of the upper apex 112U are also laser cut from circular tubing, however instead of a standard radial cut (directly along the direction of a radial line emanating from the center of the circular tubing) the inner surfaces 311, 321 are created by making an angled slot 250 using a skewed angle laser cut to form the struts 310, 320 which are connected to or emanating from the upper apex 112U to which both struts connect.

The skewed angle cut is made at an angle α as shown in FIG. 2C. While the skewed angle cut is shown as maintaining a predetermined set angle as the cut progresses from an upper apex (e.g., 112U) to a lower apex (e.g., 112L), persons skilled in the art will recognize that the strut cut could be made such that angle α changes along the strut from the upper apex to the lower apex. For example, the upper apex could have the extreme angle α as shown in FIG. 2C at the upper apex and may proportionally according to distance and angle (or by a non-linear ratio of strut distance to angle)) transition to a standard radial cut for the strut surfaces 311, 321 at their respective lower apexes (e.g., 112L).

Figure 3A:
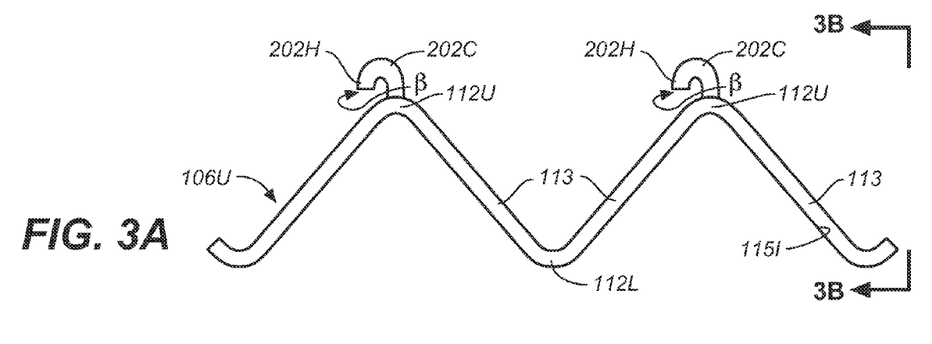
FIG. 3A is a schematicized laid flat interior view of the upper spring attachment element shown in FIG. 2A after deployment.
Figure 3B:
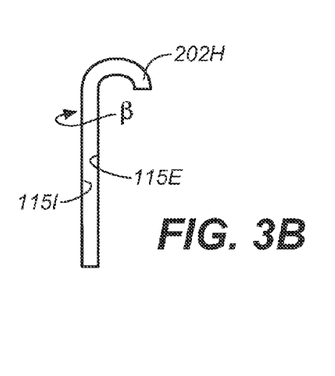
FIG. 3B is a schematicized end view of the upper spring attachment element shown in FIG. 3A.
Figure 3C:
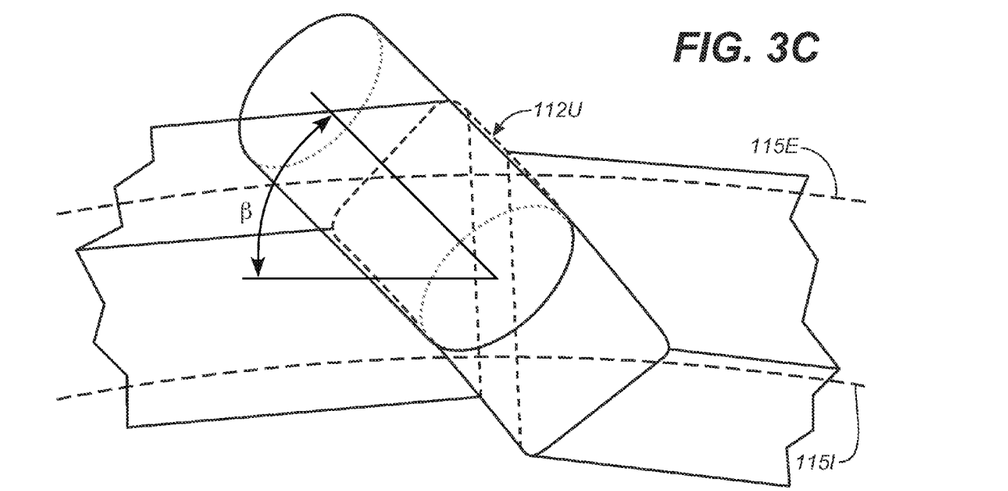
FIG. 3C is an after deployment top plan view of one upper apex 112U of upper spring attachment element 106U of FIGS. 3A and 3B including a self-flaring, active, hooked fixation element.
Figure 3D:
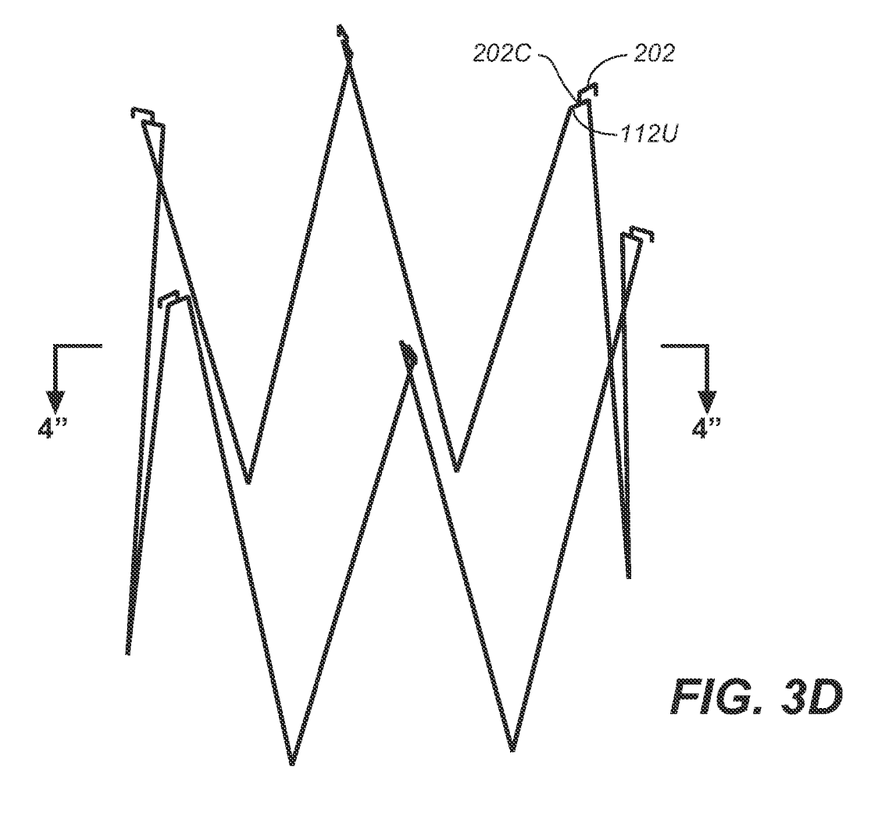
FIG. 3D is a schematicized perspective view of the upper spring attachment element shown in FIG. 2A after deployment.
Figure 3E:
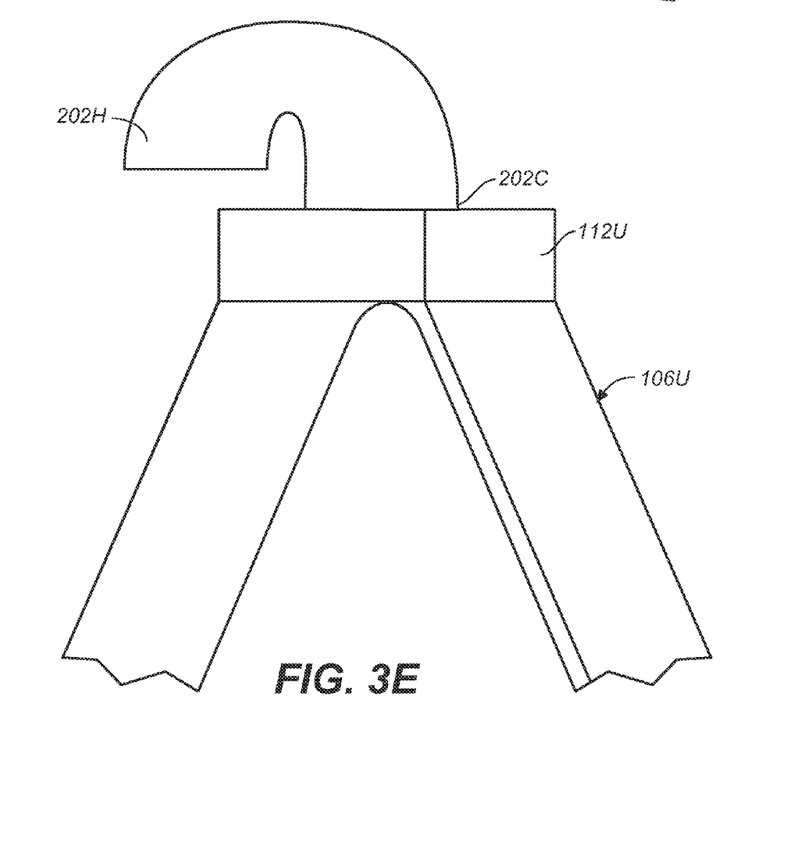
FIG. 3E is a schematicized side view of the upper apex shown in FIG. 3C.

Further, FIG. 3A is a schematicized after deployment, flat-layout interior view of upper spring attachment element 106U of stent graft 100 including self-flaring, active, hooked fixation elements 202. FIG. 3B is an after deployment end view in the direction of 3B-3B of upper spring attachment element 106U shown in FIG. 3A. FIGS. 3C, 3D, and 3E are after deployment, top, schematicized perspective, and partial inside views of one upper apex 112U of the upper spring attachment element 106U of FIGS. 3A and 3B.

Referring to FIGS. 1, 3A-E together, after deployment within body vessel 102, where stent graft 100 is in an expanded configuration, each hooked fixation element 202 is coupled at coupling-end 202C to one upper apex 112U of upper spring attachment element 106U such that hook-end portion 202H of hooked fixation element 202 is rotated (flared) outwardly by an apical twisting angle β from a second space defined by the interior side 115I and the exterior side 115E of expanded upper spring attachment element 106, as shown in FIG. 3C.

As described more fully with reference to FIG. 4 below, in one example, when coupled to upper apexes 112U of upper spring attachment element 106U, hooked fixation elements 202 twist so as to rotate about upper apexes 112U when stent graft 100 is expanded for deployment. When so configured at full deployment, hooked fixation elements 202 partially penetrate body vessel 102 and effect active fixation of stent graft 100 at its position of deployment.

In one example, the designed characteristic of upper apexes 112U to twist is enhanced by fabricating upper spring attachment element 106U from a material having a thermally-activated shape memory, such as, for example, heat-set nickel-titanium alloys,(nitinol), well know to those of skill in the art. Enhanced rotational twisting of upper apexes 112U, expressed as an outward rotation of hooked fixation elements 202 at deployment of stent graft 100 within the thermally-activating environment of a relatively warm body vessel 102, is accomplish through use of material such as nitinol as specifically engineered by shape setting and compressing. The thermal activation is an option not a requirement of working embodiments.

Figure 4:
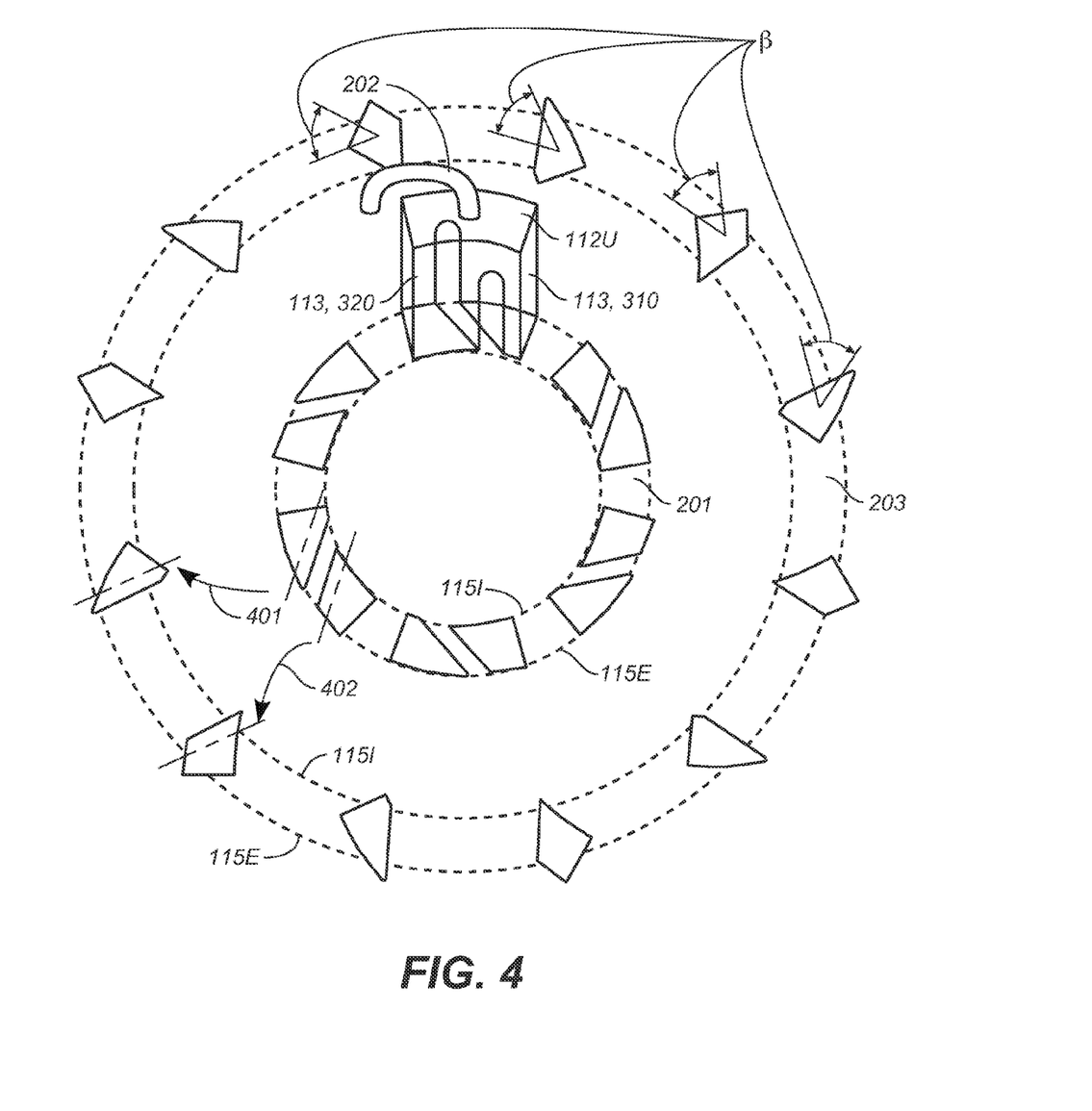
FIG. 4 shows a schematicized comparison of a before deployment configuration of compressed upper spring attachment element of FIG. 2D taken at line 4'-4', to an after deployment configuration of expanded upper spring attachment element 106U of FIG. 3D taken at line 4"-4"; and schematic illustration of one upper spring attachment element and its 3D relationship to the cross sections.

More particularly, the inner circle of FIG. 4 shows a before deployment, schematicized cross-sectional view of struts attached to a compressed upper spring attachment element 106U taken along the plane illustrated by the line 4'-4' of FIG. 2D. The outer circle of FIG. 4 is an after deployment, schematicized cross sectional view of struts (e.g., 310, 320) attached to an expanded upper spring attachment element 106U taken along the plane illustrated by the line 4"-4" of FIG. 3D.

As can be seen in the inner circle of FIG. 4, the upper apexes 112U of upper spring attachment element 106U (illustrated by the 3D-like stick like figure of one upper apex with struts attached of the upper spring attachment element— where the struts are shown tied into the cross sectional shape shown around the inner circle) lie essentially within first space 201, defined by the annular shape of upper spring attachment element 106U, as represented by partial circle dashed lines. Interior side 115I of upper spring attachment element 106U and exterior side 115E of upper spring attachment element 106U bound first space 201 defined by the annular shape of upper spring attachment element 106U.

The interior side 115I of upper spring attachment element 106U includes interior side of struts 113, (shown schematically overlain below upper apex 112U), and the interior side of upper apex 112U, struts 113 and upper apex 112U together making up a part of upper spring attachment element 106U. As described above, prior to deployment, hooked fixation element 202 (FIG. 2C) is coupled to upper apex 112U such that hooked fixation element 202 also lies within first space 201 bounded by the interior side 115I and exterior side 115I of upper spring attachment element 106U.

However, as shown in the outer circle, after radial expansion of upper spring attachment element 106U at deployment, struts 310, 320 (e.g., 113) and upper apexes 112U strain and deform, by apical twisting angle $\beta$ (several strut rotations referenced to the rotational angle $\beta$ are shown), when compared to upper apex 112U in a pre-deployment, compressed configuration shown in FIG. 2C. By twisting of the upper apex and the struts attached thereto, the potentially high localized stresses induced in struts 310, 320 and upper apex 112U during radial expansion of upper spring attachment element 106U are eliminated and such potential high peak stresses are redistributed and lowered. The direction and degree of apical twisting angle $\beta$ is controlled by adjusting the angle $\alpha$ at which the inner strut surfaces 311, 321 are cut (FIG. 2C).

FIG. 4 also shows a comparison of the before deployment configuration of compressed upper spring attachment element 106U, (shown in the inner circle), to the after deployment configuration of expanded upper spring attachment element 106U of FIG. 3A in the outer circle. As shown, in one schematically inserted apex and hook the upper apex 112U lies within first space 201 before expansion and twists and flares outwardly from second space 203 after expansion at deployment.

Arrows 401, 402 illustrate the movement of the neutral bending axis represented by substantially parallel centerlines on struts in the inner circle which rotate and separate when expanded to location and orientation (dictated by the lowest energy bending profile) in the outer circle. Knowledge of the neutral bending axis and it relation to stress and strain manipulation is well known in the art and is therefore not discussed here.

In one example, after stent graft 100 (FIG. 1) is fully expanded for deployment, either by self expansion or by application of pressure applied outwardly to the interior portion of stent graft 100, by, for example, an expansion balloon, upper spring attachment element 106U further provides a controlled frictional force between upper spring attachment element 106U and body vessel 102 interior wall. The frictional force effects both a good liquid-tight seal between stent graft 100 and body vessel 102 and passive fixation of stent graft 100 at its location of deployment.

Thus, as shown in FIGS. 1 and 2C, prior to deployment, hooked fixation elements 202, and more particularly hook-end portions 202H, lie within first space 201, defined by the annular shape of compressed upper spring attachment element 106U of stent graft 100. Said another way, hook-end portions 202H may be considered essentially tangent to the tubular shape of stent graft 100. Hook-end portions 202H neither flare inwardly not outwardly from second space 203 defined by the expanded tubular shape of stent graft 100.

Further, as shown in FIG. 3C, after placement and deployment in body vessel 102, hooked fixation elements 202 and more particularly hook-end portions 202H, flare outwardly from second space 203, defined by the annular shape of expanded upper spring attachment element 106U, and partially penetrate body vessel 102.

Body vessel 102 typically includes three layers, namely an inner intima layer 102A, an intermedia layer 102B enveloping inner init layer 102A, and an outer adventitia layer 102C enveloping intermedia layer 102B. When it is said that hooked fixation elements 202 partially penetrate a body vessel 102, it is meant that hook-end portions 202H completely penetrate inner intima layer 102A and intermedia layer 102B, but only partially penetrate outer adventitia layer 102C. Said another way, hook-end portions 202H terminate within outer adventitia layer 102C of body vessel 102.

Although hooked fixation elements are described above, in light of this disclosure, it is understood that fixation elements formed according to the present invention may be of shapes other than hooks. Further, an alternatively shaped fixation element may be attached to spring attachment elements coupled to locations on the stent graft other than at its upper end. For example, they could be coupled to a lower end of stent graft 100 (e.g., FIG. 1) opposite the upper end of stent graft 100. This disclosure provides exemplary embodiments according to the present invention. Numerous variations, whether explicitly provided for by the specification or implied by the specification or not, such as variations in structure, dimension, type of material and manufacturing process may be implemented by one of skill in the art in view of this disclosure and the embodiments described therein.

The invention claimed is:

1. A structure for fixation of a stent graft to a body vessel comprising:
    hollow cylindrically shaped stent graft elements;
    an upper spring attachment element having a hollow cylindrical shape of serpentine pattern and coupled to one of said stent graft elements, said upper spring attachment element comprising:
        upper apexes;
        lower apexes; and
        struts interconnecting said upper apexes and said lower apexes, each of said struts having an inner strut surface facing an adjacent strut extending from a common one of the upper apexes;
    hooked fixation elements having hook-end portions and coupling-ends, each of said coupling-ends coupled to one of said upper apexes;
    wherein said upper apexes including said hook-end portions lie within a compressed stent cylinder wall space projection bounded by an interior side of said upper apexes and an exterior side of said upper apexes when said stent graft is compressed prior to deployment of said stent graft in said body vessel, said inner strut surfaces having an angle that is skewed from a radius of said hollow cylindrical shape in a plane perpendicular to a stent graft central axis; and
    wherein said struts twist to cause said upper apexes including said hook-end portions to rotate outwardly from an expanded stent cylinder wall space projection bounded by said interior side of said upper apexes and said exterior side of said upper apexes to act as a hook element to penetrate said body vessel when said stent graft is expanded at deployment.

2. The structure of claim 1 wherein said stent graft elements are laser cut.

3. The structure of claim 1 wherein said upper spring attachment element is laser cut.

4. The structure of claim 1 wherein said upper spring attachment element comprises a material having shape memory.

5. The structure of claim 4 wherein said material having shape memory comprises a nickel-titanium alloy.

6. The structure of claim 1 wherein said hook-end portions terminate bluntly.

7. The structure of claim 1 wherein said hook-end portions terminate at a point.

8. The structure of claim 1 wherein said hook-end portions terminate at an angle.

9. The structure of claim 1 wherein said hook-end portions partially penetrate said body vessel at deployment of said stent graft.

10. The structure of claim 1 wherein said upper spring attachment element provides a radial biasing force directed outwardly from said stent graft central axis.

11. The structure of claim 10 wherein said radial biasing force provides passive fixation of said stent graft when said stent graft is expanded at deployment.

12. The structure of claim 1 further including tubular shaped stent graft material coupled to said stent graft elements.

13. The structure of claim 1 wherein said struts further comprise interior sides and exterior sides.

14. The structure of claim 13 wherein said inner strut surfaces extend between said interior sides and said exterior sides.

15. The structure of claim 1 wherein a cross section of said struts in said plane perpendicular to said stent graft central axis is a trapezoid.

16. The structure of claim 15 where a longest side of said trapezoid forms said inner strut surface of said strut.

17. The structure of claim 16 wherein said struts resist deformation at said longest side of said struts thus causing said struts to have said twist when said stent graft is expanded at deployment.

18. The structure of claim 1 wherein said inner strut surfaces of adjacent struts extending from a common one of the upper apexes are parallel to one another when said stent graft is compressed prior to deployment of said stent graft in said body vessel.

19. The structure of claim 1 wherein said hook-end portions are aligned with said upper apexes when said stent graft is compressed prior to deployment of said stent graft in said body vessel, said hook-end portions remaining aligned with said upper apexes when said stent graft is expanded at deployment.

\* \* \* \* \*